United States Patent
Itou et al.

(10) Patent No.: US 11,819,227 B2
(45) Date of Patent: Nov. 21, 2023

(54) TREATMENT METHOD, SEPARATION METHOD, AND FILTER ASSEMBLY

(71) Applicant: TERUMO KABUSHIKI KAISHA, Tokyo (JP)

(72) Inventors: Yoshitaka Itou, Fuji (JP); Shinya Matsumoto, Tokyo (JP); Shota Ishii, Fujinomiya (JP); Tadahiro Motomura, Fujinomiya (JP); Yoshiyuki Saito, Tokyo (JP); Aiko Sakimoto, Chigasaki (JP); Takenari Ito, Fujinomiya (JP); Haruhiko Takahashi, Tokyo (JP); Tetsuya Fukuoka, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 447 days.

(21) Appl. No.: 16/817,003

(22) Filed: Mar. 12, 2020

(65) Prior Publication Data
US 2020/0289135 A1    Sep. 17, 2020

(30) Foreign Application Priority Data

Mar. 12, 2019 (JP) .................. 2019-044690
Feb. 19, 2020 (JP) .................. 2020-026583

(51) Int. Cl.
*A61B 17/22* (2006.01)
*A61M 1/36* (2006.01)
(Continued)

(52) U.S. Cl.
CPC .......... *A61B 17/22* (2013.01); *A61M 1/3627* (2013.01); *A61M 1/3693* (2013.01);
(Continued)

(58) Field of Classification Search
CPC .......... A61M 25/104; A61M 2025/105; A61M 1/3627; A61M 1/3693; A61M 2025/0004;
(Continued)

(56) References Cited

U.S. PATENT DOCUMENTS

| | | | |
|---|---|---|---|
| 5,152,743 A | 10/1992 | Gorsuch et al. | |
| 5,527,292 A * | 6/1996 | Adams .............. | A61M 25/0172 600/585 |

(Continued)

FOREIGN PATENT DOCUMENTS

| | | |
|---|---|---|
| CN | 101132830 A | 2/2008 |
| CN | 103732271 A | 4/2014 |

(Continued)

OTHER PUBLICATIONS

European Search Report dated Aug. 5, 2020, by the European Patent Office in corresponding European Patent Application No. 20162680.1-1115. (4 pages).

(Continued)

*Primary Examiner* — Susan S Su
*Assistant Examiner* — Ted Yang
(74) *Attorney, Agent, or Firm* — BUCHANAN INGERSOLL & ROONEY PC

(57) ABSTRACT

Provided are a treatment method, a separation method, and a filter assembly capable of preventing so-called "Blue Toe syndrome" which is so-called cholesterol crystal embolism of which a fat-soluble compound such as cholesterol crystals generated during dilation of a stenosed site causes clogging in glomeruli of peripheral capillaries or kidney, acute renal failure, and the like. Cholesterol crystals generated from plaque during use of a balloon catheter are taken out of the body and removed using a centrifugal separation device or (Continued)

a filter, and usable living cells are returned to the body to reduce blood transfusion and reduce cholesterol crystal embolism.

7 Claims, 7 Drawing Sheets

(51) Int. Cl.
*A61M 25/10* (2013.01)
*A61M 25/00* (2006.01)
(52) U.S. Cl.
CPC . *A61M 25/104* (2013.01); *A61B 2017/22079* (2013.01); *A61B 2017/22081* (2013.01); *A61B 2017/22084* (2013.01); *A61M 2025/0004* (2013.01); *A61M 2025/105* (2013.01); *A61M 2202/08* (2013.01); *A61M 2205/7545* (2013.01)
(58) Field of Classification Search
CPC ...... A61M 2202/08; A61M 2205/7545; A61M 2202/046; A61M 1/3496; A61M 1/3696; A61M 2202/0427; A61B 17/22; A61B 2017/22079; A61B 2017/22081; A61B 2017/22084; A61B 2017/22001; A61B 2017/22002; B04B 5/0442; B04B 2005/045; B04B 2005/0471
See application file for complete search history.

(56) References Cited

U.S. PATENT DOCUMENTS

| | | | |
|---|---|---|---|
| 5,976,388 A | 11/1999 | Carson | |
| 6,334,842 B1 | 1/2002 | Hlavinka et al. | |
| 2002/0065507 A1* | 5/2002 | Zadno-Azizi | A61B 17/12109 604/509 |
| 2003/0055398 A1* | 3/2003 | Imran | A61M 25/104 604/510 |
| 2003/0171765 A1* | 9/2003 | Kokate | A61M 25/104 606/159 |
| 2004/0006370 A1* | 1/2004 | Tsugita | A61B 17/12109 606/200 |
| 2006/0074474 A1* | 4/2006 | Theron | A61B 17/12136 623/1.11 |
| 2006/0206028 A1 | 9/2006 | Lee et al. | |
| 2007/0021774 A1* | 1/2007 | Hogendijk | A61M 25/104 606/200 |
| 2007/0100372 A1 | 5/2007 | Schaeffer | |
| 2009/0157160 A1* | 6/2009 | Van Der Leest | A61F 2/95 623/1.11 |
| 2009/0287166 A1* | 11/2009 | Dang | A61M 25/00 604/528 |
| 2013/0131423 A1 | 5/2013 | Wang et al. | |
| 2018/0228537 A1* | 8/2018 | Dong | A61F 2/90 |
| 2018/0339130 A1* | 11/2018 | Ogle | A61M 39/06 |
| 2019/0009063 A1* | 1/2019 | Cottone | A61L 29/145 |
| 2021/0008285 A1 | 1/2021 | Okihara | |

FOREIGN PATENT DOCUMENTS

| | | |
|---|---|---|
| JP | 2012-071046 A | 4/2012 |
| JP | 2016-073377 A | 5/2016 |
| WO | 01/010343 A1 | 2/2001 |
| WO | 02/070062 A1 | 9/2002 |
| WO | 2007/011908 A2 | 1/2007 |
| WO | 2008/028975 A1 | 3/2008 |
| WO | 2016/166765 A1 | 10/2016 |
| WO | 2017/011527 A1 | 1/2017 |
| WO | 2019/189385 A1 | 10/2019 |

OTHER PUBLICATIONS

Office Action (Communication pursuant to Article 94(3) EPC) dated Aug. 19, 2020, by the European Patent Office in corresponding European Patent Application No. 20 162 680.1-1115. (6 pages).

European Search Report dated Jul. 30, 2021, by the European Patent Office in corresponding European Patent Application No. 21158341. 4-1122. (4 pages).

Office Action (the First Office Action) dated Apr. 5, 2023, by the National Intellectual Property Administration, P. R. China in corresponding Chinese Patent Application No. 202010110480.2 and an English translation of the Office Action. (13 pages).

* cited by examiner

US 11,819,227 B2

TREATMENT METHOD, SEPARATION METHOD, AND FILTER ASSEMBLY

CROSS-REFERENCES TO RELATED APPLICATIONS

This application claims priority to Japanese Application No. 2019-044690 filed on Mar. 12, 2019, the entire content of which is incorporated herein by reference.

FIELD OF THE INVENTION

The present invention generally relates to a treatment method of removing a fat-soluble compound in blood from a body, a separation method, and a filter assembly used for the treatment or the separation.

BACKGROUND DISCUSSION

Cholesterol which is a fat-soluble compound obtained by dissociation from low density lipoprotein (LDL) and crystallization is accumulated as plaque and causes arteriosclerosis.

Cholesterol crystal embolism (CCE) is a phenomenon in which plaque in a blood vessel is ruptured due to catheter treatment or the like, and needle-like cholesterol crystals having a diameter of 55 to 200 µm are diffused into a body as described in Journal of the Japanese Society of Internal Medicine, Vol 99, No. 5, p 944, which results in occlusion or inflammatory response in micro blood vessels such as peripheral blood vessels.

Specifically, there are reports of cerebral infarction, necrosis of the intestinal tract, and the like, in addition to Blue Toe syndrome due to occlusion of peripheral arteries and acute renal failure due to occlusion of glomeruli. In particular, when the fat-soluble compound is a cholesterol crystal, not only ostial occlusion but also inflammatory reaction occurs.

Furthermore, although mechanism is not known as disclosed in Journal of the American Heart Association URL: https://www.crd.york.ac.uk/PROSPERO. Unique identifier: CRD42018099447. (J Am Heart Assoc. 2018; 7:e011245. DOI: 10.1161/JAHA.118.011245.), it has been reported that when a paclitaxel drug-coated balloon catheter (paclitaxel drug is an anticancer drug) is used in a lesion area of the lower limb, mortality after three to five years is increased.

Since it is not effective for treatment of the lesion area if drug applied to the lesion area is peeled off and flows out into blood, it is preferable that the drug is eliminated from the body.

As a separation method of blood components, U.S. Pat. No. 6,334,842 discloses a method of separating platelets, white blood cells, red blood cells, and plasma by a continuous centrifugal separation device based on relative density and size.

Alternatively, as disclosed in Apheresis Manual, Revision 3 (2010), pp. 259 to 264, an LDL adsorption column method, a plasma exchange method, or the like has been proposed or performed in order to improve atherosclerosis obliterans (ASO) or improve familial cholesterolemia.

SUMMARY

When a fat-soluble compound such as a cholesterol crystal flows out from a lesion area and is accumulated on a peripheral side, it takes several months for the fat-soluble compound to vanish by metabolism. The crystals occlude peripheral capillaries. In addition, when finer crystals pass through the capillaries and circulate from a vein to the whole body, for example, clogging occurs in glomeruli having a hole diameter of about 0.01 to 0.02 m. When cholesterol causes an inflammatory response in glomeruli and the like, acute nephritis or acute renal failure may occur, which leads to renal failure. Further, paclitaxel crystals may similarly cause clogging in glomeruli and the like.

The device disclosed in U.S. Pat. No. 6,334,842 can treat hypercholesterolemia by removing the LDL by separating blood cells or separating plasma. However, U.S. Pat. No. 6,334,842 does not disclose separation of the fat-soluble compound released by catheter treatment, particularly, separation of the cholesterol crystals. Therefore, it is particularly difficult for the device disclosed in U.S. Pat. No. 6,334,842 to separate blood cells and fat-soluble compound crystals having the same size as the blood cells from each other.

A treatment method disclosed here includes: placing a distal end opening portion of a first catheter that has the distal end opening portion, a proximal end opening portion, and a lumen communicating between the distal end opening portion and the proximal end opening portion, at least at a lesion area in a blood vessel and/or in the vicinity of the lesion area; and removing a fat-soluble compound released into the blood vessel in the placing step from the distal end opening portion of the first catheter and taking the fat-soluble compound out of the body from the proximal end opening portion through the lumen.

The treatment method may further include: placing a second catheter having a treatment portion, a distal end opening portion, and a proximal end opening portion at the lesion area through the lumen of the first catheter; operating the treatment portion of the second catheter to treat the lesion area; and taking in the fat-soluble compound released by the treatment from the distal end opening portion of the second catheter and taking the fat-soluble compound out of the body from the proximal end opening portion of the second catheter through the lumen of the second catheter.

In the treatment method, the fat-soluble compound may be a cholesterol crystal released from the lesion area.

The first catheter may be a guiding catheter, the second catheter may be a drug-coated balloon catheter, and the fat-soluble compound may contain at least one of paclitaxel crystals, everolimus crystals, biolimus crystals, sirolimus crystals, and tacrolimus crystals that flow out of the lesion area when the lesion area is treated.

A separation method according to another aspect of the disclosure includes: preparing a first mixed solution containing two or more living cells having different relative densities and/or sizes; mixing the first mixed solution and two or more fat-soluble compounds having different sizes to obtain a second mixed solution; taking out at least a part of the second mixed solution; separating the second mixed solution into a third mixed solution having a concentration of the fat-soluble compound higher than that of the second mixed solution and a fourth mixed solution having a concentration of the fat-soluble compound lower than that of the second mixed solution based on a difference in relative density between the living cells and the fat-soluble compound; and separating the third mixed solution into a fifth mixed solution having a concentration of the fat-soluble compound higher than that of the third mixed solution and a sixth mixed solution having a concentration of the fat-soluble compound lower than that of the third mixed solution based on a difference in size between the living cells and the fat-soluble compound.

The separation method may further include a second mixing step of mixing the first mixed solution with at least one of the fourth mixed solution and the sixth mixed solution.

In the separation method, the first mixed solution may be blood, and the fat-soluble compound may contain at least one of cholesterol crystals, paclitaxel crystals, everolimus crystals, biolimus crystals, sirolimus crystals, and tacrolimus crystals.

A filter assembly according to aspect of the disclosure includes: a first filter that removes, from a mixed solution of two or more living cells having different sizes and two or more fat-soluble compounds having different sizes, at least a part of the fat-soluble compounds, in which the first filter has a plurality of first holes, and at least 90% or more of the first holes have a hole diameter larger than the largest living cell among the living cells and smaller than the largest fat-soluble compound among the fat-soluble compounds.

The filter assembly may further include a second filter, in which the second filter may have a plurality of second holes, and at least 90% or more of the second holes may have a hole diameter larger than the minimum deformation diameter of the living cells and smaller than the hole diameter of the first holes, and may have an average linear distance shorter than the maximum hole diameter of the first holes, the minimum deformation diameter may be the minimum diameter of a cell when the cell passes through the hole while being deformed alive, and the average linear distance may be the maximum length of a rod-shaped crystal that passes through the hole.

The filter assembly may further include a third filter, in which the third filter may have third holes, and at least 90% or more of the third holes may have a hole diameter larger than the smallest living cell among the living cells, and larger than the minimum outer diameter of the remaining fat-soluble compounds after at least a part of the fat-soluble compounds have been removed by the second filter.

According to the disclosure here, living cells such as blood and the fat-soluble compound, particularly, the cholesterol crystals generated due to rupture of the plaque are discharged from the body, such that cholesterol crystal embolism is prevented and a burden on a patient is reduced.

DETAILED DESCRIPTION

Figure 1:
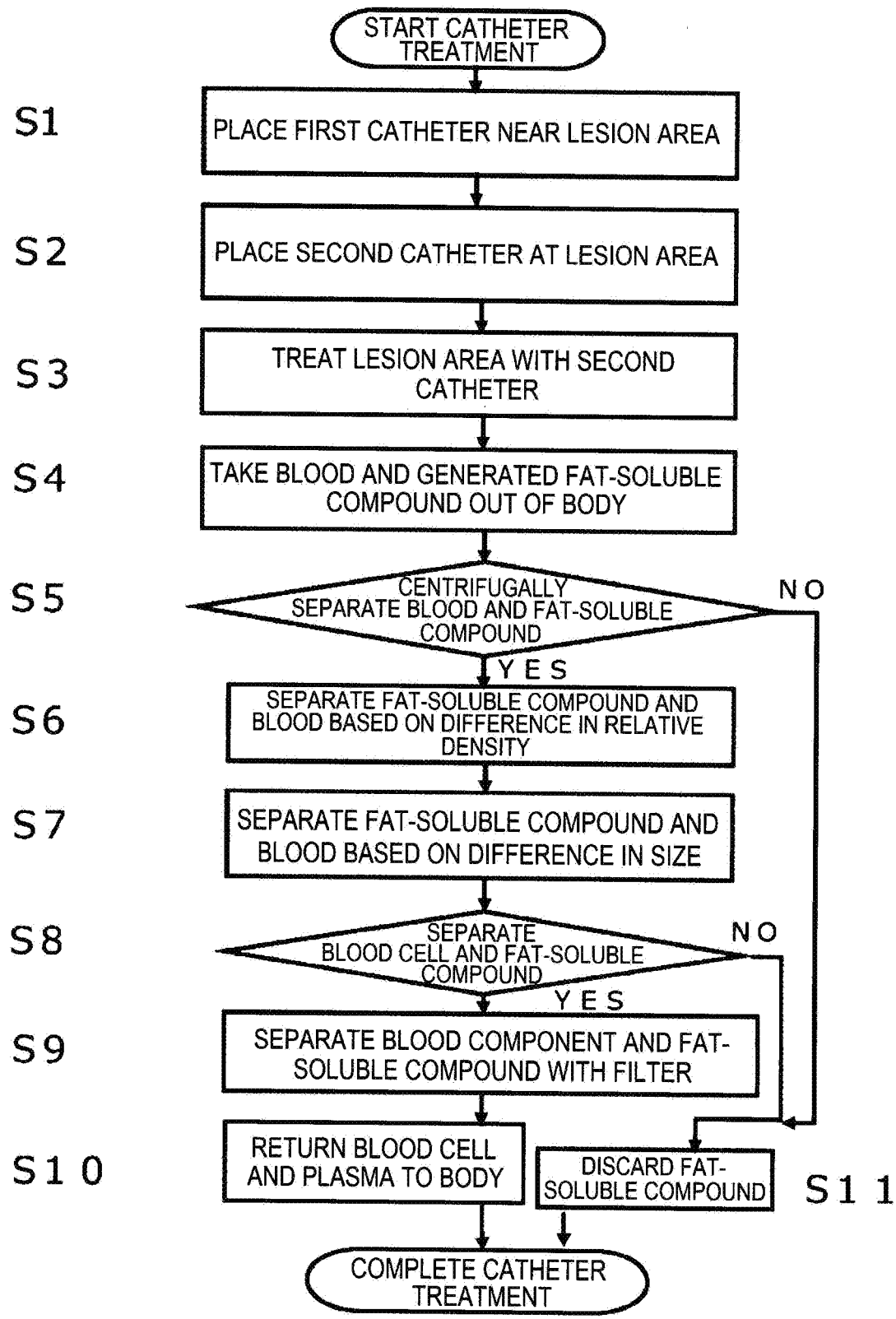
FIG. 1 is a flowchart of a treatment method according to an embodiment disclosed by way of example.

Set forth below with reference to the accompanying drawings is a detailed description of embodiments of a treatment method for removing a fat-soluble compound in blood from a body, a separation method, and a filter assembly used in the treatment and separation methods representing examples of the inventive treatment method, separation method and filter assembly disclosed here. The dimensions or scales on the drawings may be exaggerated or different from actuality/reality for convenience of description and illustration. In addition, in the following description, a proximal side of a catheter is referred to as a "proximal end", and a side inserted into a living body is referred to as a "distal end".

A treatment method disclosed here by way of example is a method used for catheter treatment. The treatment method, which is performed by steps illustrated in FIG. 1, will be described with reference to FIGS. 2 to 7.

Step S1 of placing a first catheter in the vicinity of a lesion area refers to a step of advancing a guiding catheter so that the guiding catheter distal end opening portion 11a is advanced to a position in the vicinity of the lesion area so as not to interfere with taking a balloon catheter in and out or inflation of a balloon catheter or the like, and so that the guiding catheter distal end is on the proximal side of the stenosed site or the occlusion site, which is a lesion area. In this example the lesion area or occlusion is on a blood vessel wall of a left superficial femoral artery 4. The placement of the first catheter in the vicinity of the lesion area may be accomplished by inserting a guiding catheter 11 into an artery of an arm such as a left radial artery 7 and passing the guiding catheter through the aorta 6, the aortic and iliac bifurcation 5, the left common iliac artery 1, the left iliac artery 2, and the left common femoral artery 3.

A guide wire 12 may be inserted in advance of inserting a guiding catheter and passed or conveyed through the lesion area. The lesion area may be positioned on left and right lower limb arteries, and further peripheral arteries or collateral circulation, and may be located on coronary arteries or head arteries, or the abdominal arteries such as superior mesenteric arteries, celiac arteries, or renal arteries.

Here, the lesion area refers to a stenosed site or an occlusion site caused by calcification or plaque accumulation. Placing or positioning the catheter at the lesion area includes inserting a balloon portion into a true lumen of the stenosed site by pushing a proximal portion of a treatment catheter such as a balloon catheter, and advancing the treatment catheter to a position at which dilation of the stenosed site can be accomplished so that blood flow is restored. The position to be placed may be a position where the treatment is to be performed, or a false lumen which is not limited to the true lumen.

If the lesion area is an occlusion site (i.e., a site in the blood vessel that is closed or fully blocked), placing the catheter at the lesion area means that a guide wire or a blood vessel penetrating catheter may be advanced to a position where blood flow can be restored. When an atherectomy catheter is used, placing the catheter at the lesion area means that the atherectomy catheter is advanced to a position where the occlusion site can be removed. When the catheter is placed at the lesion area, the atherectomy catheter removes the occlusion site, and then the drug-coated balloon catheter may be advanced to the lesion area in order for dilation and drug application. When the catheter is placed at the lesion area, the catheter may be once advanced and withdrawn, and placed again at an appropriate position based on a positional relationship between the blood vessel and the lesion area, such as a lesion area at a blood vessel branch portion.

Figure 2:
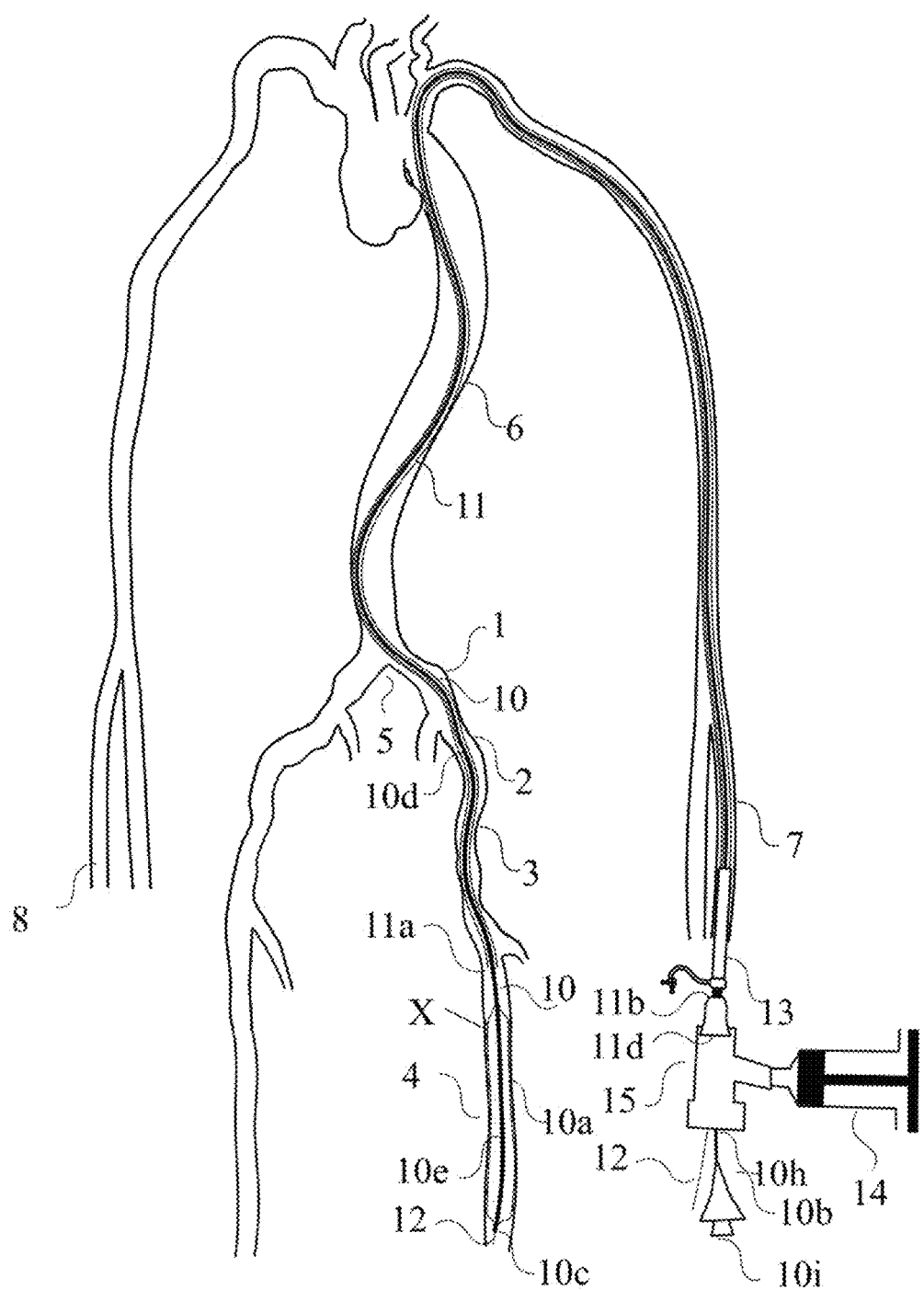
FIG. 2 is a schematic view illustrating an intravascular catheter for explaining the treatment method.

As illustrated in FIG. 2, a surgeon inserts the guiding catheter 11 as the first catheter in front of a stenosed site X along the guide wire 12, and places the guiding catheter distal end opening portion 11*a* in front of the stenosed site X (i.e., above the stenosed site in FIG. 2) of the left superficial femoral artery 4 as a first placing step.

When the plaque is ruptured and cholesterol crystals Cr are scattered in blood during this placement, a Y-connector 15 and a syringe 14 are attached to a hub 11*b* of the guiding catheter 11. Then, a tightening portion of a proximal portion of the Y-connector 15 is operated, such that the guide wire 12 (and a drug-coated balloon catheter proximal shaft 10*h*) are tightened by a silicon ring and a proximal end opening portion of the Y-connector is blocked.

The surgeon operates the syringe 14 to apply a negative pressure to a guiding catheter lumen 11*c*. The cholesterol crystals Cr are drawn into the guiding catheter distal end opening portion 11*a* by virtue of the negative pressure created by operation of the syringe, and taken out of or removed from the body through the guiding catheter lumen 11*c* and a guiding catheter proximal end opening portion 11*d* of the guiding catheter hub 11*b*. The surgeon may aspirate the cholesterol crystals Cr together with the blood from a side port of the Y-connector 15 into the syringe 14 and take the cholesterol crystals Cr and the blood out of the body.

Next, in Step S2 which involves placing a second catheter in the stenosed site, the Y-connector 15 is connected to the proximal hub 11*b* of the guiding catheter 11, a drug-coated balloon (DCB) catheter 10 as a treatment catheter is inserted into the guiding catheter 11 through the Y-connector 15, and a DCB portion 10*a* is placed at the stenosed site X as a second placing step.

The DCB catheter 10 illustrated in FIG. 2 is a rapid exchange catheter, and has a DCB distal end opening portion 10*c* most distal to the DCB portion 10*a*, and a DCB proximal end opening portion 10*d* proximal to the DCB portion 10*a*. A DCB guide wire lumen 10*f* communicated by a DCB inner tube 10*e* is provided between the DCB distal end opening portion 10*c* and the DCB proximal end opening portion 10*d*. A DCB expansion lumen 10*g* communicating with the DCB portion 10*a* communicates with the DCB proximal shaft 10*h*, and also communicates with a DCB proximal end opening portion 10*i* of a DCB proximal hub 10*b*.

The surgeon inserts a proximal portion of the placed guide wire 12 into the DCB distal end opening portion 10*c*, and inserts the DCB catheter 10 into the guiding catheter proximal end opening portion 11*d* through the Y-connector 15 along the guide wire 12. Then, the DCB portion 10*a* can be placed or positioned at the stenosed site X when the DCB portion 10*a* is further advanced with the DCB portion 10*a* protruded from the guiding catheter distal end opening portion 11*a* through the guiding catheter lumen 11*c*.

If the second catheter can release the cholesterol crystals Cr as a fat-soluble compound by treating the stenosed site X, the second catheter may be a guiding catheter, a guiding sheath, an angiographic catheter, a guide wire support catheter, or a microcatheter in addition to a treatment catheter such as a balloon catheter, a stent delivery catheter, and an atherectomy catheter, and may be an over-the-wire catheter or a rapid exchange catheter.

Alternatively, the second catheter may be a drug-coated balloon catheter carrying a drug, such as an anticancer drug or an immunosuppressive drug that can be released on a surface to prevent restenosis, or a drug-coated stent delivery catheter containing a drug in a polymer and carrying the drug on a stent surface. As the drug, anticancer drugs such as paclitaxel and immunosuppressant drugs such as everolimus, biolimus, sirolimus, and tacrolimus are used as fat-soluble compounds. For example, paclitaxel may be carried on a balloon surface in a crystalline state.

Here, the fat-soluble compound refers to a compound which is hardly soluble in water but which is more soluble in an organic solvent such as alcohol or acetone, and specifically, a compound in which a dissolved amount (g) of ethanol is greater than that of water per 100 g of solvent at room temperature, more specifically, a compound generated in the body or administered into the body, particularly refers to a crystal, or a compound present in blood, in the vicinity of cells, or in organs, in a solid state for a long period of time.

Alternatively, the second catheter is not particularly limited as long as the fat-soluble compound flows out into the blood vessel by placing and operating an intravascular filter, a thrombus removal device, a guide wire, or the like, in the blood vessel.

When the second catheter is an over-the-wire drug-coated balloon catheter, the proximal portion of the catheter has a bifurcated hub. The hub has a guide wire port that is a proximal end opening portion communicating with a distal end of the guide wire lumen along a long axis, and an expansion port that is provided on a side surface of the hub and communicating from the expansion lumen.

Figure 3A:
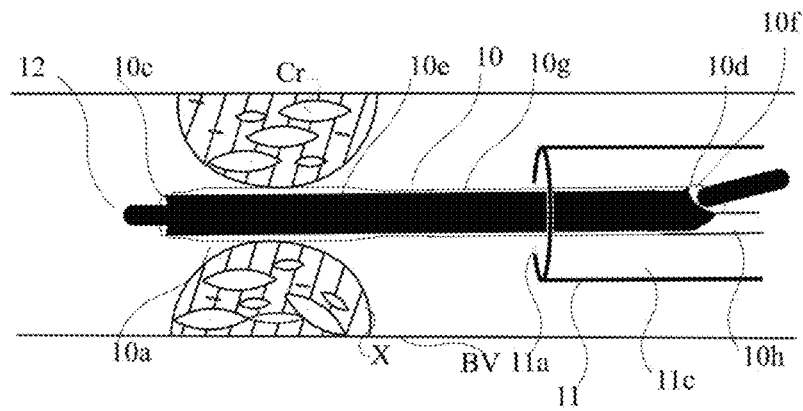
FIG. 3A is a schematic cross-sectional view illustrating a state in which a balloon catheter is placed in a stenosed site.
Figure 3B:
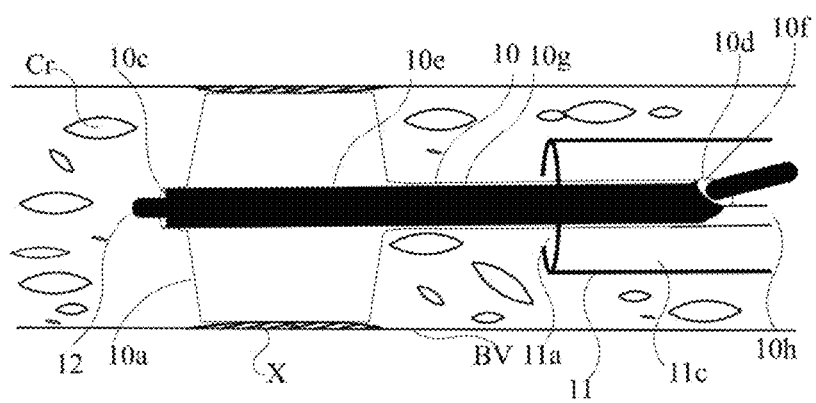
FIG. 3B is a schematic cross-sectional view illustrating a state in which plaque of a stenosed site is ruptured due to inflation of a balloon and cholesterol crystals are dispersed in a blood vessel.
Figure 3C:
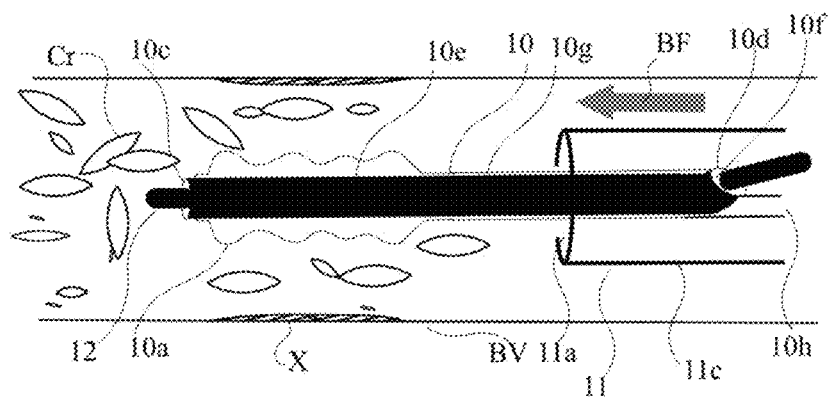
FIG. 3C is a schematic cross-sectional view illustrating a state in which blood flow is restored due to deflation of the balloon and the cholesterol crystals flow out to a peripheral side of the blood vessel due to the blood flow.

In Step S3 of treating the stenosed site with the second catheter, as illustrated in FIG. 3A, the guide wire 12 is placed to pass through the stenosed site X containing the cholesterol crystals Cr, and the rapid exchange DCB portion 10*a* is placed at the stenosed site X along the guide wire 12. When the stenosed site is dilated by inflating the DCB portion 10*a* by an inflator (not illustrated) attached to the proximal hub 10b, the plaque is ruptured and the cholesterol crystals Cr are released into the blood vessel as illustrated in FIG. 3B. Generally, the inflator is operated to reduce a pressure to the DCB portion and when the DCB portion 10a is deflated after drug is applied as illustrated in FIG. 3C, blood flow BF is restored, and simultaneously, the plaque content such as cholesterol crystals Cr flows out to the peripheral side. Alternatively, paclitaxel crystals (not illustrated) that are coated on the surface of the DCB portion 10a but remain on the surface and are not transferred to the blood vessel wall, or a drug that is applied to the blood vessel wall but does not permeate the blood vessel wall may flow out to the peripheral side.

Next, Step S4 of taking the blood and the generated fat-soluble compound out of the body is performed. In Step S4, the fat-soluble compound released into the blood vessel in a treating step is drawn into the distal end opening portion of the second catheter, passes through the second catheter lumen, and passes through the proximal end opening portion of the second catheter to be taken out of the body from the blood vessel.

In the present embodiment, in FIG. 2, the Y-connector 15 is attached to the proximal end opening portion of the hub 11b and an aspiration device is attached to the side port. The syringe 14 is an example of the aspiration device that may be used. The tightening portion of the proximal portion of the Y-connector 15 is operated, such that the guide wire 12 and the DCB proximal shaft 10h are tightened by a silicon ring and the proximal end opening portion of the Y-connector is blocked. The syringe 14 is operated to apply a negative pressure to the guiding catheter lumen 11c.

Figure 4A:
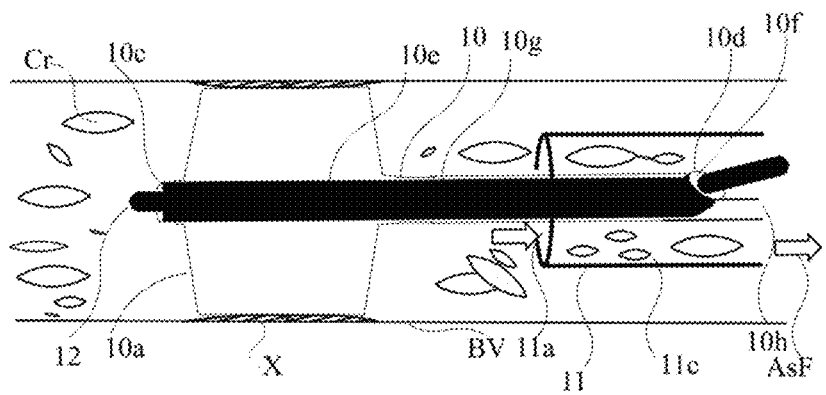
FIG. 4A is a schematic cross-sectional view illustrating a state in which cholesterol crystals in the stenosed site close to a heart are aspirated and collected by a guiding catheter.

An aspiration force AsF is generated due to the negative pressure, as illustrated in FIG. 4A. Thus, at least the cholesterol crystals Cr positioned at a proximal side of the DCB portion 10a blocked by the inflated DCB portion 10a to the guiding catheter distal end opening portion 11a, in other words, from the DCB portion 10a to the stenosed site X close to (upstream) the heart are aspirated. The aspirated cholesterol crystals Cr, which pass through the guiding catheter lumen 11c and the hub 11b from the guiding catheter distal end opening portion 11a, are stored in the syringe 14. With these operations, the fat-soluble compound such as cholesterol crystals Cr can be taken out of the body.

Figure 4B:
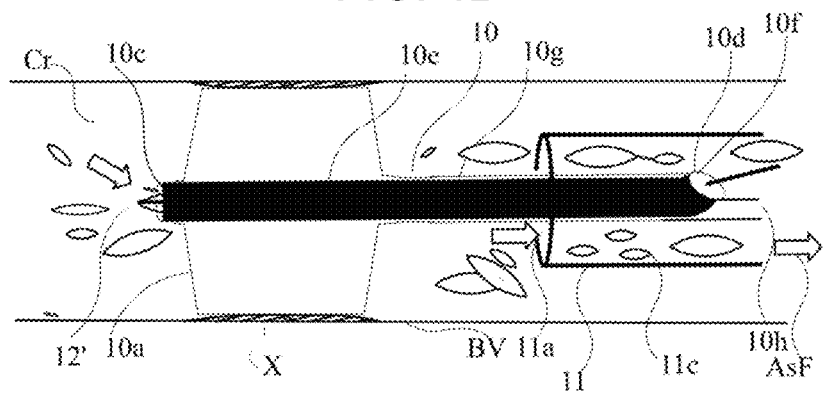
FIG. 4B is a schematic cross-sectional view of a first modification example, which illustrates a state in which cholesterol crystals in the stenosed site close to a periphery, which pass through a distal end opening portion of a guide wire lumen of a rapid exchange balloon catheter, and cholesterol crystals close to the heart, which pass through a distal end opening portion of a guiding catheter, are simultaneously aspirated using a guide wire which has a small outer diameter.

As a first modification example, when the DCB catheter 10 is applied with a thinner (smaller outer diameter) guide wire 12', for example, a guide wire lumen 10f having an inner diameter of 0.018 inches (0.46 mm) as illustrated in FIG. 4B, the guide wire 12' having a smaller outer diameter of 0.014 inches (0.36 mm) is placed at the stenosed site. Thus, the DCB catheter 10 is placed along the thin guide wire 12', and the cholesterol crystals Cr in the stenosed site X close to (downstream) the periphery or debris of the stenosed site, the flown-out excess drugs, and the like can be aspirated through a gap between the guide wire 12' and the guide wire lumen 10f. Thus, in this first modification example, instead of the cholesterol crystals Cr and the like flowing (being aspirated) between the interior surface of the guiding catheter and the outer surface of the second catheter as described above, the cholesterol crystals Cr and the like flow (are aspirated) between the interior surface of the guide wire lumen and the outer surface of the guide wire.

Figure 4C:
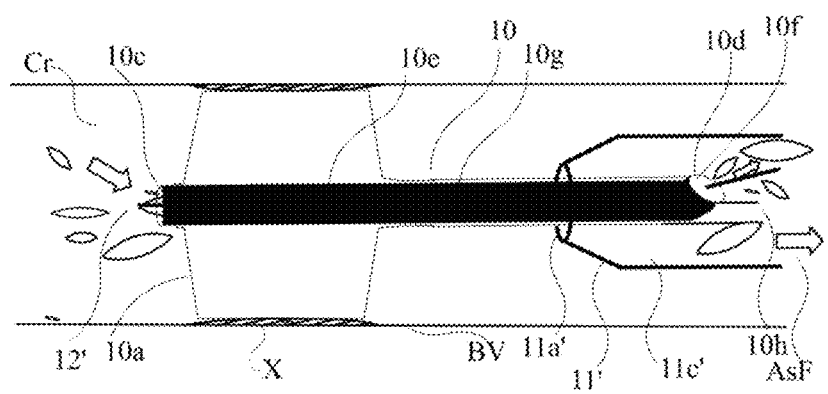
FIG. 4C is a schematic cross-sectional view of a second modification example, which illustrates a state in which fat-soluble compound crystals distal of the stenosed site passing through a distal end opening portion of a guide wire lumen of a rapid exchange balloon catheter are aspirated using a guide wire having a small outer diameter and a guiding catheter of a distal opening portion having a small inner diameter.

As a second modification example, if a guiding catheter 11' having a smaller inner diameter of the distal end opening portion is used so that the drug-coated balloon portion 10a can pass therethrough before inflation as illustrated in FIG. 4C, an amount aspirated into a guiding catheter distal end opening portion 11a' is decreased. Therefore, the cholesterol crystals Cr on the distal side of the stenosed site X or the debris of the stenosed site, and the flown-out excess drugs can be more efficiently aspirated.

The guiding catheter 11' having a small diameter of the distal end opening portion may be exchanged with the guiding catheter 11, or may be inserted into the lumen of the guiding catheter 11 and protruded from the guiding catheter distal end opening portion 11a, or may use a rapid exchange guiding catheter. When the DCB portion 10a after inflation, that is, after the drug is applied to the stenosed site X, cannot pass through the lumen of the guiding catheter 11', the inflated DCB catheter 10 and the guiding catheter 11' after the treatment are simultaneously removed from the body.

Figure 5A:
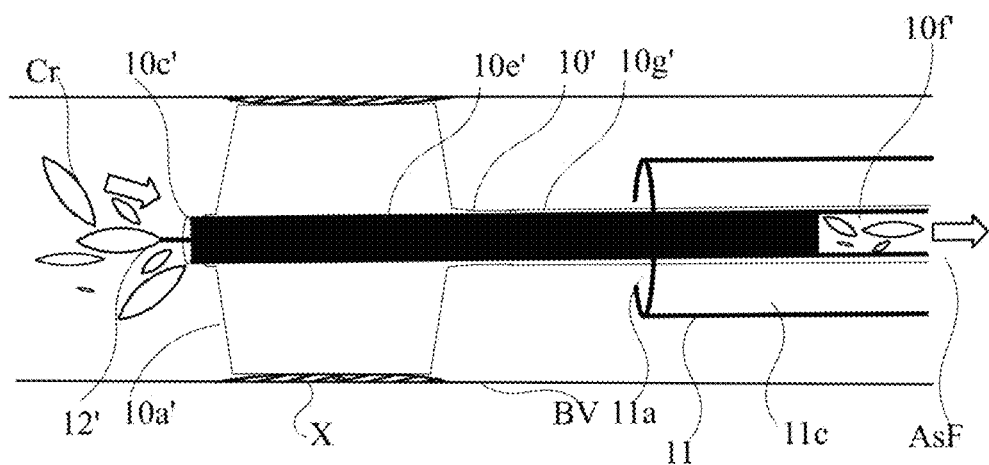
FIG. 5A is a schematic cross-sectional view of the third modification example, which illustrates a state in which the excessive fat-soluble compound crystals distal of the stenosed site passing through the distal end opening portion of the guide wire lumen of an over-the-wire drug-coated balloon catheter are aspirated using the guide wire having a small outer diameter.

As a third modification example, the second catheter may use an over-the-wire DCB catheter 10' as illustrated in FIG. 5A. If the catheter is the over-the-wire DCB catheter 10', for example, when a guide wire lumen 10f is used with a guide wire having a diameter of 0.035 inches (0.9 mm), it is easy to exchange the guide wire with a guide wire having a diameter of 0.018 inches or 0.014 inches. Therefore, it is possible to attach a Y-connector 15' and a syringe 14' to the hub communicating with the guide wire lumen 10f and aspirate the cholesterol crystals Cr on the distal side of the stenosed site X. At this time, the cholesterol crystals Cr distal of the stenosed site X may be aspirated by the syringe 14 attached to the guiding catheter 11 having different flow paths.

Figure 5B:
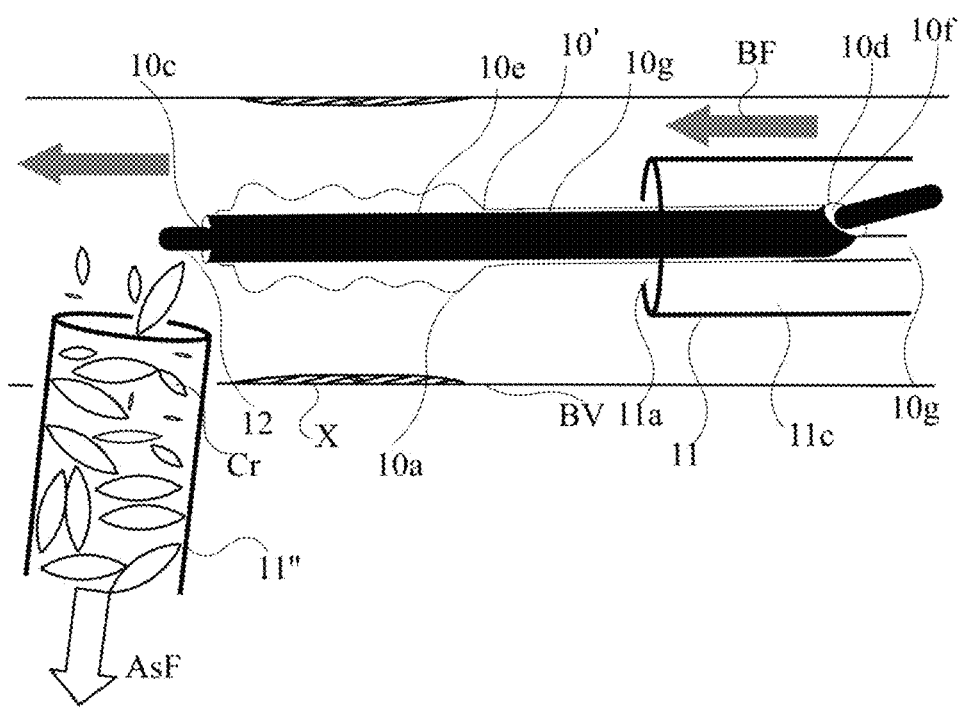
FIG. 5B is a schematic cross-sectional view of the fourth modification example which illustrates a state in which the blood flow is restored due to deflation of the balloon and the cholesterol crystals that have flowed out are aspirated and collected by a third guiding catheter placed on the distal side of the blood vessel due to the blood flow.

As a fourth modification example, a third guiding catheter 11" is inserted so that the distal open end of the third catheter 11" is at a position distal of the stenosed site X, and after the drug-coated balloon portion 10a is deflated, the cholesterol crystals Cr flown out to the peripheral side by the restored blood flow BF may be aspirated by the third guiding catheter 11", as illustrated in FIG. 5B Alternatively, puncture is performed at the stenosed site X close to the periphery, the guide wire 12, the guiding catheter 11, and the drug-coated balloon catheter 10 are placed, and the cholesterol crystals Cr flown out by the treatment, and the like may be aspirated using the guiding catheter 11 or the drug-coated balloon catheter 10 which is placed on the peripheral side. A puncture position of the guiding catheter 11" may be an ipsilateral puncture on the same leg as that having the stenosed site X or may be a contralateral puncture on a leg opposite from the leg having the stenosed site X. In terms of aspiration, a guiding catheter introduced from the blood vessel of an arm including the radial arteries, may be used as the third guiding catheter 11".

Next, Step S5 of determining whether to separate the blood and the fat-soluble compound is performed.

The cholesterol crystal Cr, which is the fat-soluble compound that has been aspirated, also contains blood or calcified debris, and clot AG such as thrombus, which are aspirated together. However, if the aspiration amount is decreased, the aspirated cholesterol crystal Cr and blood may be discarded, in consideration of costs for separation and reducing the patient burden, as they are together with red blood cells RBC, white blood cells WBC, platelets PLT, and plasma Pla as blood cell components in blood.

On the other hand, when there is a large amount of plaque in an abdominal aorta, or when the cholesterol crystals Cr are easily isolated due to the use of a thrombolytic agent or the like, saline may be injected at the stenosed site X to separate the blood and the cholesterol crystals Cr from each other, whereby usable blood cell components or plasma Pla may return to the body.

Alternatively, when an amount of blood to be separated is large, such as when the cholesterol crystals Cr cannot be aspirated during the catheter treatment, when cholesterol crystal embolism is developed after the catheter treatment, or when the cholesterol crystals Cr are separated during the catheter treatment, it is more preferable to separate the cholesterol crystals Cr and the like from the usable blood components. This is to prevent GVHD complications due to blood transfusion when a bleeding amount is large.

When it is determined that the blood and the fat-soluble compound should not be centrifugally separated from each other, the process proceeds to Step S11 of discarding the blood together with the fat-soluble compound, and the catheter treatment is completed.

When it is determined that living cells and the fat-soluble compound should be separated from each other, that is, when it is determined that the blood and the cholesterol crystals Cr should be separated from each other, the process proceeds from Step S5 to a separating step.

Generally, plasma Pla has a relative density of 1.02 to 1.03, platelets PLT have a relative density of about 1.04 and a diameter of 1 to 2 µm, white blood cells WBC have a relative density of 1.05 to 1.09 and a diameter of 10 to 20 µm, and red blood cells RBC have a relative density of 1.08 to 1.10 and a diameter of 7 to 10 µm.

On the other hand, if the cholesterol crystal Cr is larger than LDL, the cholesterol crystal Cr has a diameter of 0.01 to 300 µm, a length of 0.05 to 1000 µm, and a relative density of about 1.05, and when a ratio of the maximum length to the maximum diameter in one crystal is defined as an aspect ratio, the aspect ratio is 1 or more and less than 10.

In this separation method, blood containing platelets PLT, white blood cells WBC, red blood cells RBC, and plasma Pla as two or more living cells having different relative densities and/or different sizes before the catheter treatment is obtained as a first mixed solution, and blood with which two or more fat-soluble compounds having different sizes released by the catheter treatment, for example the cholesterol crystals Cr having different sizes are mixed as a mixing step is defined as a second mixed solution. The whole or at least a part of the second mixed solution is taken out, but it is preferable to take out the second mixed solution simultaneously with the catheter treatment or within 24 hours after completion of the catheter treatment.

Next, as a first separating step shown in step S6 of FIG. 1, the second mixed solution is centrifugally separated to obtain two mixed solutions. The two mixed solutions are a third mixed solution having a concentration of the cholesterol crystal Cr higher than that of the second mixed solution and a fourth mixed solution having a concentration of the cholesterol crystal Cr lower than that of the second mixed solution. This separation of the second mixed solution into the third and fourth mixed solutions is based on a difference in relative density.

In a case of the present embodiment, the centrifugal separation device can separate a mixed solution of the cholesterol crystals Cr and the blood which is the second mixed solution into a low relative density layer, a high relative density layer, and a medium relative density layer, based on a difference in relative density. As between the three layers, the low relative density layer has a lower relative density than the medium relative density layer, and the medium relative density layer has a lower relative density than the high relative density layer. The mixed solution is separated into a component containing a large amount of the plasma Pla as a low relative density layer, a component containing a large amount of the red blood cells RBC as a high relative density layer, a component containing the cholesterol crystals Cr, the platelet PLT having a small difference in relative density, and a large amount of the white blood cells WBC as a medium relative density layer.

In the first separating step shown in S6, the low relative density layer and the high relative density layer are collected as a fourth mixed solution having a concentration of the cholesterol crystal lower than that of the second mixed solution, and the medium relative density layer is separated and collected as the third mixed solution having a concentration of the cholesterol crystal higher than that of the second mixed solution.

Next, as a second separating step shown as S7 in FIG. 1, the blood cells and the cholesterol crystals Cr contained in the third mixed solution are separated based on a difference in size thereof.

The third mixed solution is separated in a chamber provided with step portions making a flow rate different based on a difference in size of the blood cells and the cholesterol crystals Cr. Since a flow rate of the smallest platelets PLT is high, the platelets PLT flow out from the chamber first. Next, the white blood cells WBC flow out, and then the cholesterol crystals Cr larger than the white blood cells WBC and having a lower flow rate finally flow out from the chamber. Thus, the third mixed solution can be separated into a fifth mixed solution having a cholesterol concentration higher than that of the third mixed solution and a sixth mixed solution having a cholesterol concentration lower than that of the third mixed solution. The fifth mixed solution contains a large amount of cholesterol crystals Cr, and the sixth mixed solution corresponds to a mixed solution containing a large amount of platelets PLT or containing a large amount of white blood cells WBC.

Figure 6:
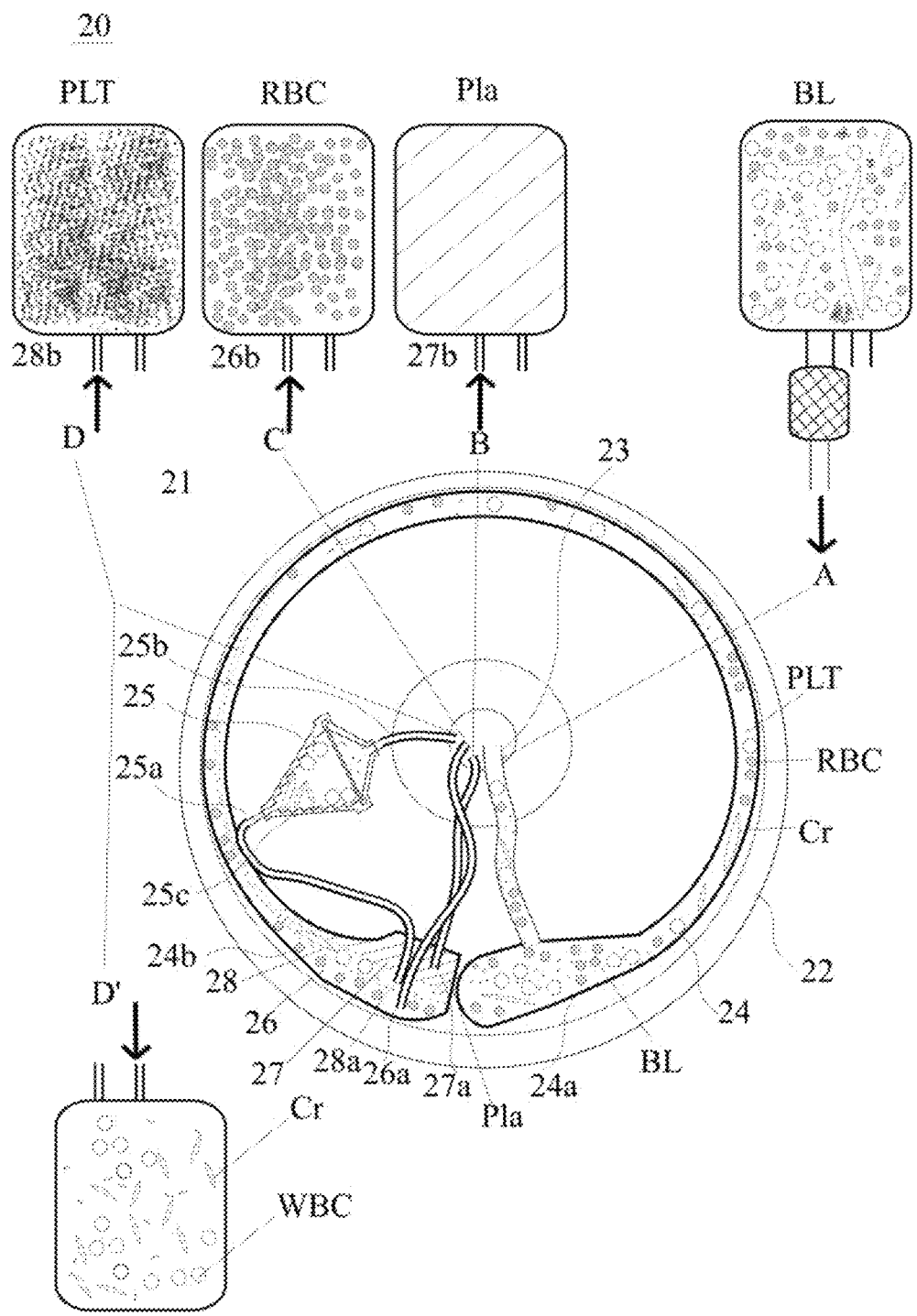
FIG. 6 is a schematic cross-sectional view of a part of a centrifugal separation device used in a separation method according to an embodiment of the present invention.

In the present embodiment, the blood cells, the plasma Pla, the cholesterol crystals Cr, and the like are separated by a continuous centrifugal separation system 20 illustrated in FIG. 6. When a blood amount is small, a batch type centrifugal separation device may be used. FIG. 6 is a schematic view of a centrifugal separation part of a blood component centrifuge Spectra Optia (registered trademark) manufactured by TERUMO BCT, INC. A device 21 is provided with a rotating portion 22, an inflow pipe 23, a separation container 24, and a fluid chamber 25.

As a first separating step, blood containing the cholesterol crystals Cr corresponding to the second mixed solution which flows into the separation container 24 from the inflow pipe 23 is formed by a high relative density layer 26 and a low relative density layer 27 which correspond to the fourth mixed solution having a cholesterol concentration lower than that of the second mixed solution due to a centrifugal force, and a medium relative density layer 28 which corresponds to the third mixed solution having a cholesterol concentration higher than that of the second mixed solution for the fluid chamber 25.

The fluid chamber 25 is provided with a fluid chamber inflow portion 25a and a fluid chamber outflow portion 25b, and is provided with step portions 25c separated based on a size. The continuous centrifugal separation system 20 is provided with a high relative density layer outflow pipe 26a and a high relative density layer storage container 26b, a low relative density layer outflow pipe 27a and a low relative density layer storage container 27b, and a medium relative density layer outflow pipe 28a and a medium relative density layer storage container 28b, into which the separated blood components are flow. The middle relative density layer outflow pipe 28a is connected to the fluid chamber inflow portion 25a, and the medium relative density layer storage container 28b is connected to the fluid chamber outflow portion 25b.

Since the mixed solution of blood BL containing the blood cell components and the cholesterol crystals Cr flowing from the inflow pipe 23 at the center is stored in the separation container 24, the rotating portion 22 is rotated by a motor (not illustrated) or the like, and the centrifugal force is thus applied. Each blood cell component, the cholesterol crystals Cr, and the plasma Pla in the mixed solution are separated based on a difference in relative density while the mixed solution flows from a separation container inlet side 24*a* toward a separation container outlet side 24*b*.

Separation conditions may be appropriately set according to a blood amount, a flow rate, and a size of the centrifuge. This device can separate the blood components by applying the centrifuge force of 0 to 1200 G at the flow rate of higher than 0 and 142 ml/min and a rotational speed in a range from 0 to 3000 rpm.

The blood cells and the cholesterol crystals Cr can be separated due to a difference in relative density, but thrombus, the clot AG (debris), and large cholesterol crystal Cr are removed in advance by a pre-filter or the like having a hole diameter larger than that of blood cells, such that the blood amount can be reduced to increase an efficiency during centrifugal separation.

In the present embodiment, conditions are shown in which the plasma Pla is aggregated in the low relative density layer 27, the red blood cells RBC as living cells are aggregated in the high relative density layer 26, and the platelets PLT, the white blood cells WBC and cholesterol crystals Cr are aggregated in the medium relative density layer 28. The conditions in this case depend on a composition of the blood components and the blood amount, but when an amount of mixed solution is 400 ml, for example, it is preferable that the flow rate is preferably 10 to 130 ml/min and the rotational speed is 100 to 2500 rpm.

The low relative density layer 27 passes through a flow path B connected with a tube or the like, and flows into the low relative density layer storage container 27*b* using a pump or the like to be stored therein as it is. The high relative density layer 26 passes through a flow path C connected with a tube or the like, and flows into the high relative density layer storage container 26*b* to be stored therein as it is. Alternatively, the platelets PLT, the white blood cells WBC, and the cholesterol crystals Cr may be separated based on a difference in each of the relative densities by changing the centrifugal separation conditions.

Next, as a second separating step, Step S7 of separating the fat-soluble compound and the blood based on a difference in size is performed.

In the present embodiment, the medium relative density layer 28 mainly containing a large amount of the platelets PLT, the cholesterol crystals Cr, and the white blood cells WBC flows into the fluid chamber 25 through the fluid chamber inflow portion 25*a*, the medium relative density layer 28 being the third mixed solution having a concentration of the cholesterol crystal higher than that of the second mixed solution.

The flown-in medium relative density layer 28 is separated based on a size of the step portion 25*c*, the smallest platelet PLT flows out first, passes through a flow path D, and flows into the medium relative density layer storage container 28*b* to be stored therein. Further, since the cholesterol crystals Cr larger than the white blood cells WBC are retained in the inflow portion 25*a* of the fluid chamber 25 at an outer periphery of the step portion 25*c*, and the white blood cells WBC are aggregated in the outflow portion 25*b*, the white blood cells WBC and the cholesterol crystals Cr can be separated.

Since the largest white blood cell WBC and the cholesterol crystals Cr in the blood cell have a small difference in relative density and difference in size as compared with other blood cells, the separation container 24 and the like may be washed with saline or the like after collecting the platelets PLT and collected without separating. If the cholesterol crystals Cr are not sufficiently separated from the blood cell component or the plasma Pla, centrifugal separation may be further performed.

Here, Step S8 involves determining whether to separate the blood cells and the fat-soluble compound, in other words, a determination is made as to whether usable blood cell components are to be returned to the body.

In Step S6 which is the first separating step, the fourth mixed solution not containing the cholesterol crystals Cr or being separated based on the relative density and/or the size and containing the cholesterol crystals Cr within an allowable range is separated. In Step 8, the determination may be made as to that the plasma Pla and the red blood cells RBC corresponding to the fourth mixed solution is returned to the body.

In the second separating step S7, of the platelets PLT, the white blood cells WBC, or the like, which is the sixth mixed solution separated and collected from the medium relative density layer 28, the platelets PLT, the white blood cells WBC, or the like which is not activated and does not contain the cholesterol crystals Cr is treated with autologous blood is separated. In Step 8, and thus it may be returned, or a second mixing step of mixing with the first mixed solution may be performed. In the second mixing step, specifically, at least one of the fourth mixed solution and the sixth mixed solution may be returned to the blood, which is the first mixed solution, in the blood vessel in the body.

When a large amount of cholesterol crystals Cr remains, the blood may be discarded. However, if it is necessary to maintain the patient's immunity, such as when a drug that reduces the white blood cells WBC is administered, Step S9 of separating the blood components and the fat-soluble compound by a filter is performed. Alternatively, in order to further separate a minute amount of cholesterol crystals Cr, the cholesterol crystals Cr having no difference in relative density or size may be further removed from the plasma Pla and the red blood cells RBC, which are a fourth mixed solution having a low concentration of the cholesterol crystals, separated in the first separating step, or the platelets PLT and the white blood cells WBC, which are the sixth mixed solution, separated in the second separating step, using a filter assembly illustrated in FIG. 7.

Figure 7:
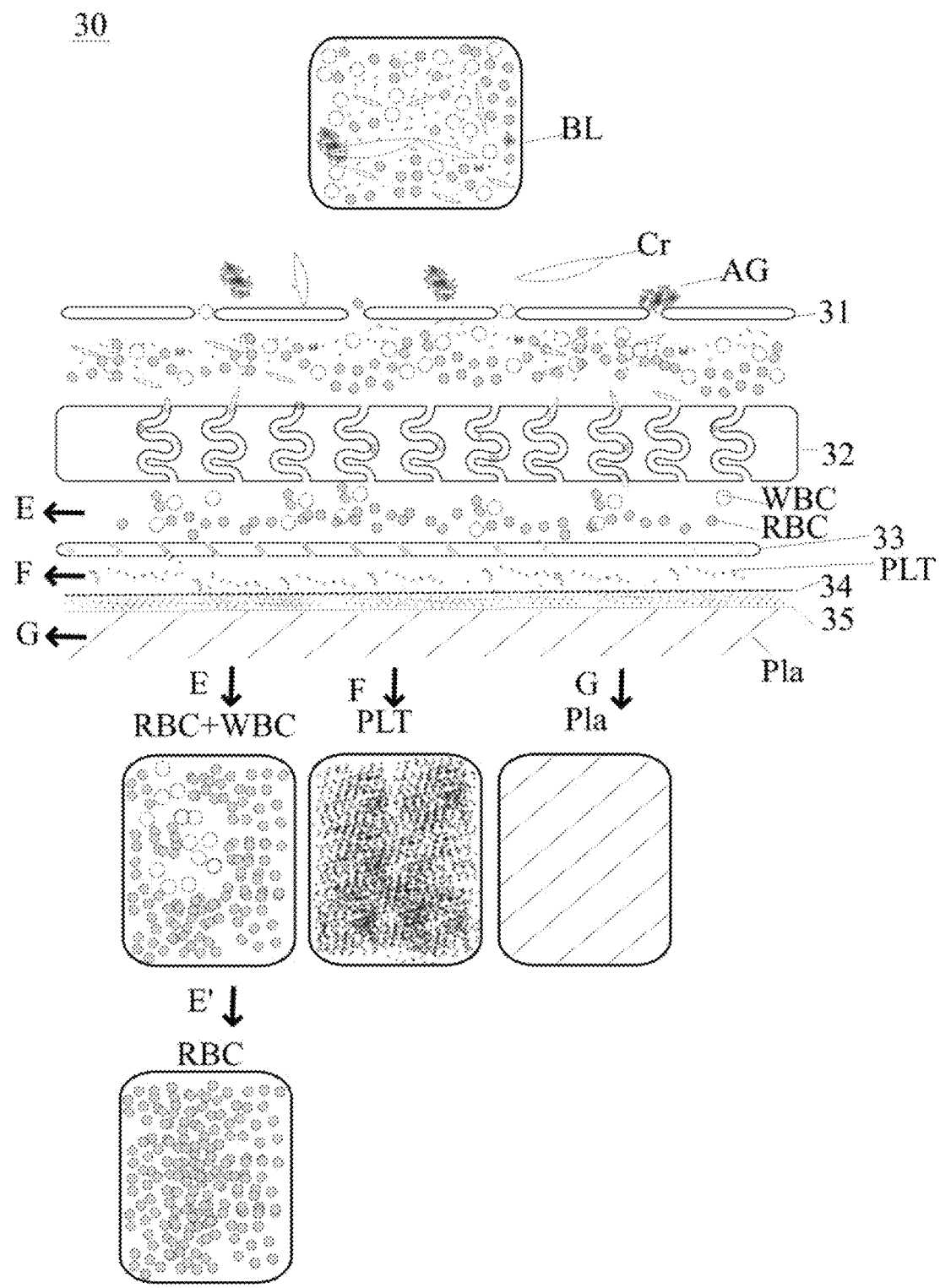
FIG. 7 is a schematic cross-sectional view of a filter assembly according to an embodiment of the present invention.

FIG. 7 is a schematic view of a filter assembly 30. The filter assembly 30 has at least a first filter 31, and may have a second filter 32, a third filter 33, a fourth filter 34, and a fifth filter 35 each of which has different hole diameters or hole diameter distributions, if necessary. The filter may be a flat plate, a hollow fiber, or a pleated structure having three-dimensional folds, but a flat plate form is preferred. Alternatively, a plurality of filters having the same hole diameter or hole diameter distribution may be used. Alternatively, in order to efficiently remove a larger crystal or thrombus which is a cell agglutinate to prevent clogging, a filter having a larger hole diameter may be used as a pre-filter.

The filter may be made of a nonwoven fabric using a polymer resin, a porous film formed from a polymer solution by a phase transition method, or a microporous film formed from melt-forming by a stretching method. As a material, a polyester resin, a polyurethane resin, a polyamide resin, or polyolefin resins such as polyethylene resin and polypropylene resin, a silicone resin, or a fluororesin such as a polytetrafluoroethylene resin, or elastomers, polymer alloys, and block copolymers thereof, and the like may be used.

Alternatively, the filter may be one in which a circular hole is formed in a metal plate by a laser or the like, but an inlet of the hole may be an elliptical shape, an oval shape, a spindle shape, or a simple slit. A non-circular hole is preferred to allow the living cells that are easily deformed to easily pass through and prevent the hard and elongated cholesterol crystals Cr having a large aspect ratio from passing therethrough.

Although the hole diameter may be constant in a thickness direction of the filter, it is preferable that a filter has a short average linear distance in order to prevent the cholesterol crystals Cr that are easy to pass through the blood cell and have a large aspect ratio from passing through the hole. The average linear distance corresponds to the maximum length of a rod-shaped crystal that can pass through the hole. For example, when piercing the filter with a laser, the filter may be one in which a depth of the hole is changed or an angle of the hole is changed. If the material of the filter is a metal, an existing material used for medical care may be used, but for example, SUS304 or SUS316 as a stainless alloy, or a nickel titanium alloy or a cobalt chromium alloy may be used, and a combination of a resin and a metal may be used.

The filter may further include a filter having a housing and an inlet port and an outlet port of the blood. If the fat-soluble compound can be separated by an adsorbent, the filter may be used in combination with a column having an adsorbent such as activated carbon or an ion exchange resin.

In a mixture of the fat-soluble compound generated by the catheter treatment and the blood cells or a mixture of the cell agglutinate such as thrombus, at least a part of the fat-soluble compound are removed by the first filter 31.

The first filter 31 has first holes, and at least 90% or more of the first holes have a hole diameter larger than the largest white blood cell WBC among the living cells, smaller than the thrombus or the like which is the smallest cell agglutinate, and smaller than the largest fat-soluble compound among the fat-soluble compounds such as cholesterol crystals Cr.

Here, the hole diameter of the filter may be measured by any method, but values of the hole diameter, the maximum hole diameter, the average hole diameter, and the hole diameter distribution measured with a porosity meter in accordance with JIS K3832 can be used. As the hole diameter of the filter, for example, a value measured with a porous meter 1500A manufactured by PMI may be used.

The maximum hole diameter of the first hole in the first filter 31 is preferably 30 μm or less, and the minimum hole diameter thereof is 1 μm or more. As the material of the first filter 31, a nonwoven fabric made of a polyethylene terephthalate resin is particularly preferable. The first filter 31 can remove most of the cholesterol crystals Cr that may occlude arterioles having an inner diameter of at least about 0.1 to 0.2 mm.

Alternatively, a filter for separating a mixture of the white blood cells WBC and the cholesterol crystals Cr in which most of the platelet PLT and the red blood cells RBC have been already separated in Steps S6 and S7 may be a combination of filters having different hole diameter distributions, for example, a combination of a filter having a hole diameter of 5 to 30 μm and a filter having a hole diameter of 10 to 20 μm. Thereby, the cholesterol crystal Cr slightly larger than the white blood cell WBC and the cholesterol crystal Cr slightly smaller than the white blood cell WBC can be efficiently removed.

The second filter 32 provided on a downstream side of the first filter 31 of the filter assembly 30 has second holes, and at least 90% or more of the second holes may have a hole diameter larger than the minimum deformation diameter of the living cell, for example, the red blood cell RBC. At least 90% or more of the second holes have a hole diameter larger than the maximum outer diameter of the remaining fat-soluble compound crystals after at least a part of the fat-soluble compound crystals Cr having a large length and a large diameter have been removed by the first filter 31, and has an average linear distance shorter than the maximum length.

Here, the minimum deformation diameter refers to the minimum diameter of a living cell when the cell passes through the hole while being deformed, and the minimum deformation diameter of the red blood cell RBC is, for example, 4 to 6 μm. Further, the average linear distance refers to the maximum length of a rod-shaped crystal that can pass through the hole. If the cholesterol crystals Cr can be removed, the average linear distance is 1 to 1000 μm, and preferably 10 to 100 μm.

Specifically, the maximum hole diameter of the second holes in the second filter 32 is 20 μm or less, and the minimum hole diameter thereof is 0.1 μm or more. Further, the average linear distance is preferably 9 μm or more and less than 200 μm, and a ratio of the average linear distance to the average hole diameter (average linear distance/average hole diameter) is more preferably 1 or more and less than 10.

Alternatively, at least 90% or more of the second holes may have a hole diameter larger than the minimum deformation diameter of the red blood cells RBC. In FIG. 7, the second holes in the second filter 32 have a flow path that is a non-linear and meanders in the filter. Therefore, it becomes difficult for the second hole to pass the cholesterol crystals Cr that has a large aspect ratio and is hard to be deformed (not easily deformed). On the other hand, since the hole diameter is larger than the maximum diameter of the cholesterol crystals Cr, the cholesterol crystal Cr can occlude the holes and prevent the blood from flowing due to clogging.

Furthermore, since the living cells can be deformed, the living cells can pass through while deforming even if the second hole may be a non-circular shape, an elliptical shape, an oval shape, a spindle shape, or a simple slit. Even if the flow path is meandering, the blood cells flow while deforming. Therefore, the cholesterol crystal Cr having the same size and shape as the blood cell has a longer time to pass through the second filter 32 than the blood cell. Therefore, the cholesterol crystals Cr are captured by the second filter 32, and a content of the cholesterol crystals Cr in the blood can be further reduced.

The third filter 33 provided on a downstream side of the second filter 32 of the filter assembly 30 has third holes, and at least 90% or more of the third holes have a hole diameter larger than the smallest cell among the living cells, and larger than the minimum outer diameter of the remaining fat-soluble compounds after at least a part of the fat-soluble compounds have been removed by the second filter 32. More preferably, 90% of the third holes in the third filter 33 has a hole diameter of 0.5 to 2 μm.

Specifically, the third filter 33 allows the white blood cells WBC and the red blood cells RBC to hardly pass through so that few if any white blood cells WBC and red blood cells RBC pass through, but allows the platelets PLT to pass through.

The white blood cells WBC and the red blood cells RBC that can be collected from blood component E in FIG. 7 do not contain the cholesterol crystals Cr because the cholesterol crystals Cr smaller than the blood cells pass through the third filter 33.

Further, the filter assembly 30 may be provided with a fourth filter 34 having a smaller hole diameter than the minimum deformation diameter of the platelets PLT. Thereby, the cholesterol crystals Cr smaller than the platelet PLT can be removed. By removing the cholesterol crystals Cr smaller than the platelet PLT, the cholesterol crystal Cr having the maximum length of 1 μm or less can be removed from the platelet PLT collected from blood components. Thus, the cholesterol crystals Cr that are attached to the glomeruli to cause clogging when they pass through lower limb capillaries having an inner diameter of about 7 μm and flows around the whole body and then into a kidney and may cause inflammatory reaction, can be reduced.

Further, the filter assembly 30 may be provided with the fifth filter 35 in which at least 90% or more of the holes have a hole diameter larger than the low relative density lipoprotein and smaller than the platelet PLT. Thus, the cholesterol crystals Cr may be removed from the plasma Pla collected as a blood component G so that the plasma Pla containing a coagulation factor or the like may be used without being discarded.

The blood cells collected as a blood component E may be removed of the white blood cells WBC by a white blood cell removal filter, if necessary. Thereby, the blood component E may collect and contain the red blood cells RBC as a blood cell component that does not contain the white blood cells WBC.

In Step 10 of returning the blood cells and the plasma Pla to the body, the blood cells and plasma Pla with reduced cholesterol crystals Cr are returned to the body if necessary. In Step S11, the fat-soluble compound is discarded, and the catheter treatment is completed.

In the description above, cholesterol crystal Cr has been described as an example of the fat-soluble compound. However, the fat-soluble compound may be used as an anticancer drug or immunosuppressant drug applied to the drug-coated balloon catheter or a drug-coated stent, crystals of an anticancer drug or immunosuppressant drug, or a mixture containing one or more of these.

Specifically, the fat-soluble compound may be paclitaxel, cholesterol crystals, crystals of an anticancer drug or immunosuppressant drug, or a mixture containing one or more of these. If the fat-soluble compound does not contain the cholesterol crystals, examples thereof may be at least one of paclitaxel, everolimus, biolimus, sirolimus, and tacrolimus, or a mixture of crystals thereof.

Further, the combination of filters is not limited to the present embodiment, and the assembly may be a stacked body of each filter or has an independent housing for each filter, or may be only a centrifugal separation device or the filter assembly alone, or may change the orders.

In the centrifugal separation of the blood and the fat-soluble compound, the component flowing into the fluid chamber 25 may be appropriately adjusted so as to be the high relative density layer 27 or the low relative density layer 26.

The separation of the blood and the fat-soluble compound is preferably performed simultaneously with or immediately after the catheter treatment, but may be performed at least within 24 hours after completion of the catheter treatment.

When the blood is difficult to be collected, some blood may be taken out of the patient's body and stored within at least one month prior to the catheter treatment. In this case, the stored blood is returned to the patient's body after the blood containing a large amount of the fat-soluble compound generated by the catheter treatment is taken out, such that it can prevent anemia or transfusion complications, reduction in costs of drug administration, or side effects of drug administration.

Since Spectra Optia (registered trademark, blood component centrifuge) can return the blood to the body while performing centrifugal separation, for example, the blood may be returned to the body from the vein of the left arm while performing the catheter treatment in the right radial artery. If the amount of the blood taken out is small and the cholesterol crystals Cr can be removed during the treatment, the blood is injected into the catheter 11 by which the blood is taken out, and the blood is returned directly to the ischemic lower limb arteries from which the blood is taken out, which may reduce puncture areas.

Alternatively, in this treatment method, the blood cells may be washed with a saline to further remove the attached cholesterol crystals Cr.

As described above, the treatment method has been described with reference to the preferred embodiments. However, the guiding catheter 11 and the treatment catheter may be introduced from the femoral arteries, or may be introduced from the radial arteries of the arm.

The detailed description above describes embodiments of a treatment method, a separation method, and a filter assembly representing examples of the inventive treatment method, separation method, and filter assembly disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment method comprising:
   placing a distal end opening portion of a first catheter at or in a vicinity of a lesion area in a blood vessel, the first catheter being a guiding catheter comprising a proximal end opening portion and a lumen extending between and communicating the distal end opening portion and the proximal end opening portion;
   drawing into the distal end opening portion of the guiding catheter cholesterol crystals released into the blood vessel as a result of the placing of the distal end opening portion of the guiding catheter at or in the vicinity of the lesion area in the blood vessel;
   conveying the cholesterol crystals that have been drawn into the distal end opening portion of the guiding catheter along the lumen to the proximal end opening portion of the guiding catheter so that the cholesterol crystals pass through the proximal end opening portion of the guiding catheter and are removed from the body;
   introducing a distal end of a drug-coated balloon catheter into the lumen of the guiding catheter and moving the drug-coated balloon catheter along the lumen of the guiding catheter and distally beyond the distal end opening portion of the first catheter to position the drug-coated balloon catheter at the lesion area, the drug-coated balloon catheter comprising a balloon having an outer surface on which is coated a drug, a distal end opening portion, a proximal end opening portion and a lumen extending between and communicating the distal end opening portion of the drug-coated balloon catheter and the proximal end opening portion of the drug-coated balloon catheter, the drug that is coated on the outer surface of the balloon containing drug crystals that are at least one of paclitaxel crystals, everolimus crystals, biolimus crystals, sirolimus crystals and tacrolimus crystals, the drug-coated balloon catheter being moved distally beyond the distal end opening portion of the first catheter before any other catheter is moved distally beyond the distal end opening portion of the first catheter;

the introducing of the distal end of the drug-coated balloon catheter into the lumen of the guiding catheter occurring after the conveying of the cholesterol crystals that have been drawn into the distal end opening portion of the guiding catheter along the lumen of the guiding catheter to the proximal end opening portion of the guiding catheter;

inflating the balloon of the drug-coated balloon catheter after positioning the drug-coated balloon catheter at the lesion area to treat the lesion area, the inflating of the balloon resulting in release of additional cholesterol crystals, the additional cholesterol crystals being released from the lesion area; and drawing into the distal end opening portion of the drug-coated catheter: i) at least some of the drug crystals flowing out of the lesion area when the lesion area is treated; ii) at least some of the drug crystals that are not applied to a blood vessel wall of the blood vessel and that remain on the surface of the balloon after the lesion area is treated; iii) at least some of the drug crystals that are applied to the blood vessel wall as the lesion area is treated, but that do not permeate the blood vessel wall; and iv) at least some of the additional cholesterol crystals released from the lesion area; and conveying the at least some of the drug crystals flowing out of the lesion area when the lesion area is treated, the at least some of the drug crystals that are not applied to a blood vessel wall and that remain on the surface of the balloon after the lesion area is treated, the at least some of the drug crystals that are applied to the blood vessel wall as the lesion area is treated, but that do not permeate the blood vessel wall, and the at least some of the additional cholesterol crystals released from the lesion area that have been drawn into the distal end opening portion of the drug-coated balloon catheter along the lumen of the drug-coated balloon catheter for removal from the body.

2. The treatment method according to claim 1, further comprising advancing the guiding catheter along a guide wire to place the distal end opening portion of the guiding catheter at or in the vicinity of the lesion area.

3. The treatment method according to claim 1, further comprising advancing the balloon of the drug-coated balloon catheter to the lesion area in the blood vessel while the distal end opening portion of the guiding catheter is positioned at or in the vicinity of the lesion area in the blood vessel.

4. A treatment method comprising:
placing a distal end opening portion of a first catheter at or in a vicinity of a lesion area in a blood vessel, the first catheter comprising a proximal end opening portion and a lumen extending between and communicating the distal end opening portion and the proximal end opening portion;

drawing into the distal end opening portion of the first catheter a fat-soluble compound released into the blood vessel as a result of the placing of the distal end opening portion of the first catheter at or in the vicinity of the lesion area in the blood vessel;

conveying the fat-soluble compound that has been drawn into the distal end opening portion of the first catheter along the lumen to the proximal end opening portion of the first catheter so that the fat-soluble compound passes through the proximal end opening portion of the first catheter and is removed from the body;

introducing a balloon catheter into the lumen of the first catheter and moving the balloon catheter along the lumen of the first catheter to position a balloon of the balloon catheter at the lesion area, the balloon catheter comprising a distal end opening portion, a proximal end opening portion and a lumen extending between and communicating the distal end opening portion of the balloon catheter and the proximal end opening portion of the balloon catheter, the balloon catheter also comprising a balloon having an outer surface on which is coated a drug containing drug crystals, the drug crystals being at least one of paclitaxel crystals, everolimus crystals, biolimus crystals, sirolimus crystals and tacrolimus crystals, the balloon catheter being introduced into the lumen of the first catheter before any other catheter is introduced into the lumen of the first catheter;

expanding the balloon of the balloon catheter after positioning the balloon at the lesion area so that the balloon is expanded to an expanded state and so that the balloon in the expanded state contacts the lesion area and results in a release of cholesterol crystals from the lesion area;

the drawing of the fat-soluble compound into the distal end opening portion of the first catheter occurring before the expanding of the balloon of the balloon catheter into the expanded state;

drawing into the distal end opening portion of the balloon catheter: i) at least some of the drug crystals flowing out of the lesion area when the lesion area is treated; ii) at least some of the drug crystals that are not applied to a blood vessel wall of the blood vessel and that remain on the surface of the balloon after the lesion area is treated; iii) at least some of the drug crystals that are applied to the blood vessel wall as the lesion area is treated, but that do not permeate the blood vessel wall; and iv) at least some of the cholesterol crystals released from the lesion area; and conveying the at least some of the drug crystals flowing out of the lesion area when the lesion area is treated, the at least some of the drug crystals that are not applied to the blood vessel wall of the blood vessel and that remain on the surface of the balloon after the lesion area is treated, the at least some of the drug crystals that are applied to the blood vessel wall as the lesion area is treated, but that do not permeate the blood vessel wall, and the at least some of the cholesterol crystals released from the lesion area that have been drawn into the distal end opening portion of the balloon catheter along the lumen of the balloon catheter for removal from the body.

5. The treatment method according to claim 4, wherein the first catheter is a guiding catheter and further comprising advancing the guiding catheter along a guide wire to place the distal end opening portion of the guiding catheter at or in the vicinity of the lesion area.

6. The treatment method according to claim 4, wherein the drawing of the fat-soluble compound into the distal end opening portion of the first catheter occurs before the introducing of the balloon catheter into the lumen of the first catheter.

7. A treatment method comprising:
- placing a distal end opening portion of a guiding catheter at or in a vicinity of a lesion area in a blood vessel, the guiding catheter comprising a proximal end opening portion and a lumen extending between and communicating the distal end opening portion and the proximal end opening portion;
- drawing into the distal end opening portion of the guiding catheter a fat-soluble compound released into the blood vessel as a result of the placing of the distal end opening portion of the guiding catheter at or in the vicinity of the lesion area in the blood vessel;
- conveying the fat-soluble compound that has been drawn into the distal end opening portion of the guiding catheter along the lumen to the proximal end opening portion of the guiding catheter so that the fat-soluble compound passes through the proximal end opening portion of the guiding catheter and is removed from the body;
- introducing a balloon catheter into the lumen of the guiding catheter and moving the balloon catheter along the lumen of the guiding catheter to position a balloon of the balloon catheter at the lesion area, the balloon catheter comprising a distal end opening portion, a proximal end opening portion and a lumen extending between and communicating the distal end opening portion of the balloon catheter and the proximal end opening portion of the balloon catheter, the balloon catheter being introduced into the lumen of the guiding catheter before any other catheter is introduced into the lumen of the guiding catheter;
- expanding the balloon of the balloon catheter after positioning the balloon at the lesion area so that the balloon is expanded to an expanded state and so that the balloon in the expanded state contacts the lesion area and results in a release of additional fat-soluble compound;
- the drawing of the fat-soluble compound into the distal end opening portion of the guiding catheter occurring before the expanding of the balloon of the balloon catheter into the expanded state;
- drawing into the distal end opening portion of the balloon catheter a first portion of the additional fat-soluble compound that is released by the contact of the balloon in the expanded state with the lesion area and that is located on a distal side of the balloon in the expanded state and in contact with the lesion area;
- drawing into the distal end opening portion of the guiding catheter a second portion of the additional fat-soluble compound that is released by the contact of the balloon in the expanded state with the lesion area and that is located on a proximal side of the balloon in the expanded state and in contact with the lesion area;
- conveying the first portion of the additional fat-soluble compound that has been drawn into the distal end opening portion of the balloon catheter along the lumen of the balloon catheter to the proximal end opening portion of the balloon catheter so that the first portion of the additional fat-soluble compound passes through the proximal end opening portion of the balloon catheter and is removed from the body; and
- conveying the second portion of the additional fat-soluble compound that has been drawn into the distal end opening portion of the guiding catheter along the lumen of the guiding catheter to remove the second portion of the additional fat-soluble compound from the body.

* * * * *